US011591558B2

(12) United States Patent
Boitard (10) Patent No.: US 11,591,558 B2
(45) Date of Patent: Feb. 28, 2023

(54) METHOD FOR ANALYSIS AND CELL CULTURE AND AN ASSOCIATED SYSTEM (71) Applicant: MilliDrop Instruments SAS, Saint-Mandé (FR)

(72) Inventor: Laurent Boitard, Paris (FR)

(73) Assignee: EUROFINS MILLIDROP, Nantes (FR)

(*) Notice: Subject to any disclaimer, the term of this patent is extended or adjusted under 35 U.S.C. 154(b) by 560 days.

(21) Appl. No.: 16/628,329

(22) PCT Filed: Jun. 19, 2018

(86) PCT No.: PCT/EP2018/066262
§ 371 (c)(1),
(2) Date: Jan. 3, 2020

(87) PCT Pub. No.: WO2019/007674
PCT Pub. Date: Jan. 10, 2019

(65) Prior Publication Data
US 2021/0332317 A1    Oct. 28, 2021

(30) Foreign Application Priority Data
Jul. 3, 2017    (FR) .................................. 17 56264

(51) Int. Cl.
C12N 1/20    (2006.01)
C12M 1/12    (2006.01)
(Continued)

(52) U.S. Cl.
CPC ............ *C12M 25/01* (2013.01); *C12M 23/06* (2013.01); *C12M 23/44* (2013.01); *C12M 41/18* (2013.01); *C12M 41/34* (2013.01); *C12N 1/20* (2013.01)

(58) Field of Classification Search
CPC ........ C12M 25/01; C12M 23/06; C12M 23/44; C12M 41/18; C12M 41/34; C12N 1/20
(Continued)

(56) References Cited
U.S. PATENT DOCUMENTS 10,928,382 B2 * 2/2021 Konry .................... C12M 25/01
2014/0065658 A1   3/2014 Bertholle et al.

FOREIGN PATENT DOCUMENTS
GB      2 544 769        5/2017
WO    WO-2014/064359    5/2014
WO    WO-2016/198697    12/2016

OTHER PUBLICATIONS
International Search Report for Application No. PCT/EP2018/066262, dated Aug. 28, 2018 European Patent Office, Rijswikj, NL.
(Continued)

Primary Examiner — Fred Prince
(74) Attorney, Agent, or Firm — B. Aaron Schulman, Esq.; Stites & Harbison, PLLC (57) ABSTRACT The method for analysis and cell culture comprises the following steps:
  generating a train (14) of ordered drops (16) in a carrier fluid (40), the train (14) of drops (16) comprising at least one culture drop (42), the culture drop (42) comprising a culture medium (50) and at least one cell (4),
  circulating the train (14) of drops (16) in a tube (10),
  incubating the train (14) of drops (16) in the tube (10),
  measuring at least one parameter indicative of the content of the culture drop (42) in the tube (10) at different times,
  recovering the culture drop (42) at one end (36) of the tube (10),
the steps being carried out in a controlled atmosphere (6).

13 Claims, 4 Drawing Sheets (51) Int. Cl.
*C12M 3/00* (2006.01)
*C12M 1/02* (2006.01)
*C12M 1/34* (2006.01)

(58) Field of Classification Search
USPC .............................. 435/252.7, 287.1, 288.1
See application file for complete search history.

(56) References Cited

OTHER PUBLICATIONS

Written Opinion for International Search Application No. PCT/EP2018/066262, dated Jul. 3, 2017 European Patent Office, Gitschiner, Berlin.

* cited by examiner

METHOD FOR ANALYSIS AND CELL CULTURE AND AN ASSOCIATED SYSTEM

CROSS-REFERENCE TO RELATED APPLICATIONS

This application is a U.S. non-provisional application claiming the benefit of French Application No. 17 56264, filed on Jul. 3, 2017, which is incorporated herein by reference in its entirety.

FIELD OF THE INVENTION

The present invention relates to a method for cell analysis and culture.

BACKGROUND

In the field of cell culture, it is known to grow cell colonies on the plate surface comprising a growth medium gelled by a gelling agent, in particular agar-agar.

One commonly used system comprises agar-agar plates arranged in petri dishes. The individual cells are spread on the surface of the plates and multiply until forming a cell colony. The cell colonies are called clones, such colonies constituting a heap of cells coming from an individual cell.

The cells are for example microorganisms, such as bacteria, yeasts or filamentous fungi. The systems on plates make it possible to quantify and identify the cells. The cells can be identified from many methods, for example, a verification of the growth capacity of a colony on a selective medium, a selective marker, a mass spectroscopy measurement or the like. The growth of bacterial colonies on a selective medium containing an antibiotic is used, for example, to determine the resistance of a bacterium to the antibiotic.

However, certain cells must be studied under specific conditions such as an anoxic conditions. Anoxia is a decrease in the dissolved oxygen or oxygen that is present and bioavailable in the medium. For example, cells that live in extreme environments such as the bottom of an ocean, the bottom of an oil well or the intestines of an animal survive in anoxic or anaerobic environments. An "anaerobic environment" is an environment where no oxygen is present in dioxygen form. Thus, each step to cultivate or study these cells must be done under particular safety conditions so as to preserve the anaerobic nature of the environment of the cells.

It is thus known to manipulate the cells in a glove box. A glove box is a sealed enclosure that allows manipulations in a particular atmosphere. Gloves, fastened to one of the transparent walls of the enclosure, make it possible to access the inside without confinement ceasing. The operator places his hands in the gloves and then sees his manipulations through the transparent wall.

For example, in a glove box, the operator isolates cells by limit dilution in a micro-titration plate. Then, once the cells are isolated in the wells of the plate, the plate is sealed. The plate is next removed from the glove box and transferred into an incubator to allow the culture of the cells and clone formation. Following an incubation phase, the plate is next introduced again into a glove box under a controlled atmosphere and unsealed, and the clones are recovered to perform various analyses. It is known, for example, to perform clone sorting using a cytometer placed in a glove box under an anaerobic atmosphere.

However, all of these manipulations make the method very restrictive and difficult to control. Furthermore, the manipulation space in a glove box is relatively restricted, which limits the number of possible actions for the handler. Therefore, given the heaviness of the manipulations, the number of steps in a glove box is reduced as much as possible. For example, only a single measurement is done on the samples at the end of the incubation. Such manipulations therefore prevent the high-throughput analyses of cells with monitoring during the incubation.

SUMMARY

One aim of the invention is to provide a method allowing a simple isolation of cells, culturing of cells and characterization of the culture, as well as recovery for specific cell populations, while limiting the risks of contamination.

To that end, the invention relates to a method for analysis and cell culture comprising the following steps:
  generating a train of ordered drops in a carrier fluid, the train of drops comprising at least one culture drop, the culture drop comprising a culture medium and at least one cell,
  circulating the train of drops in a tube,
  incubating the train of drops in the tube,
  measuring at least one parameter indicative of the content of the culture drop in the tube at different times,
  recovering the culture drop at one end of the tube,
  the steps being carried out in a controlled atmosphere.

The method for analysis and cell culture according to the invention may comprise one or more of the following features, considered alone or according to any technically possible combination:
  the method further comprises a step for analysis of the measurements done for the culture drop, the recovery of the culture drop or the continuation of the incubation depending on the results of the analysis;
  the controlled atmosphere is an anaerobic atmosphere;
  the parameter is a parameter indicative of the growth of a clone in the culture drop;
  the method comprises a step for preparing the system in which a gas, the composition of which is controlled, is injected into the tube before the step for generating the train of drops.

The invention also relates to an analysis and cell culture system comprising:
  a tube,
  a module for generating a train of ordered drops in a carrier fluid, the train of drops comprising at least one culture drop, the culture drop comprising a culture medium and at least one cell,
  a device for circulating the train of drops in the tube,
  a device for incubating the train of drops in the tube,
  a measuring device, able to measure at least one parameter indicative of the content of the culture drop in the tube at different times,
  a device for recovering the culture drop at one end of the tube,
  a device for controlling the atmosphere able to control the atmosphere in the analysis and culture system.

The analysis and cell culture system according to the invention may comprise one or more of the following features, considered alone or according to any technically possible combination:
  the device for controlling the atmosphere comprises a chamber with a controlled atmosphere containing the generating module, the circulating device, the tube, the incubating device, the measuring device and the recovery device;

the tube is impermeable to the gases, the device for controlling the atmosphere comprising a chamber with a controlled atmosphere containing the recovery device, at least part of the tube being arranged outside the chamber with a controlled atmosphere;

the tube has a measuring area, the measuring device being able to measure the parameter indicative of the content of the culture drop at different times at the measuring area, the measuring area of the tube being placed in a chamber with a controlled atmosphere, the parts of the tubes not extending in a chamber with controlled atmosphere being covered by an impermeable sheath;

the train of drops comprises at least one drop comprising an oxygen indicator agent;

the train of drops comprises at least one drop comprising an oxygen reducing agent;

the incubating device comprises a coil able to be temperature-regulated, part of the tube being wound around the coil;

the generating module comprises:
 a reservoir comprising a suspension of cells in an anaerobic atmosphere, the reservoir being sealed by a septum,
 a collection device able to pierce the septum to collect part of the suspension;

the analysis and cell culture system comprises at least one impermeable solenoid valve able to isolate two parts of the tube from one another.

BRIEF DESCRIPTION OF THE DRAWINGS

The invention will be better understood upon reading the following description, provided solely as an example, and done in reference to the appended drawings, in which.

DETAILED DESCRIPTION

In the following description, the terms "upstream" and "downstream" and the terms "inlet" and "outlet" are used in reference to the normal circulation directions of the fluids in the system. The term "diameter" refers to the maximum span of the tube considered in a plane transverse, that is to say, perpendicular, to the central axis of the tube, for example, the diameter of a circle in the case where the transverse section of the tube is circular or the diagonal of a rectangle in the case where the transverse section of the tube is rectangular.

Figure 1:
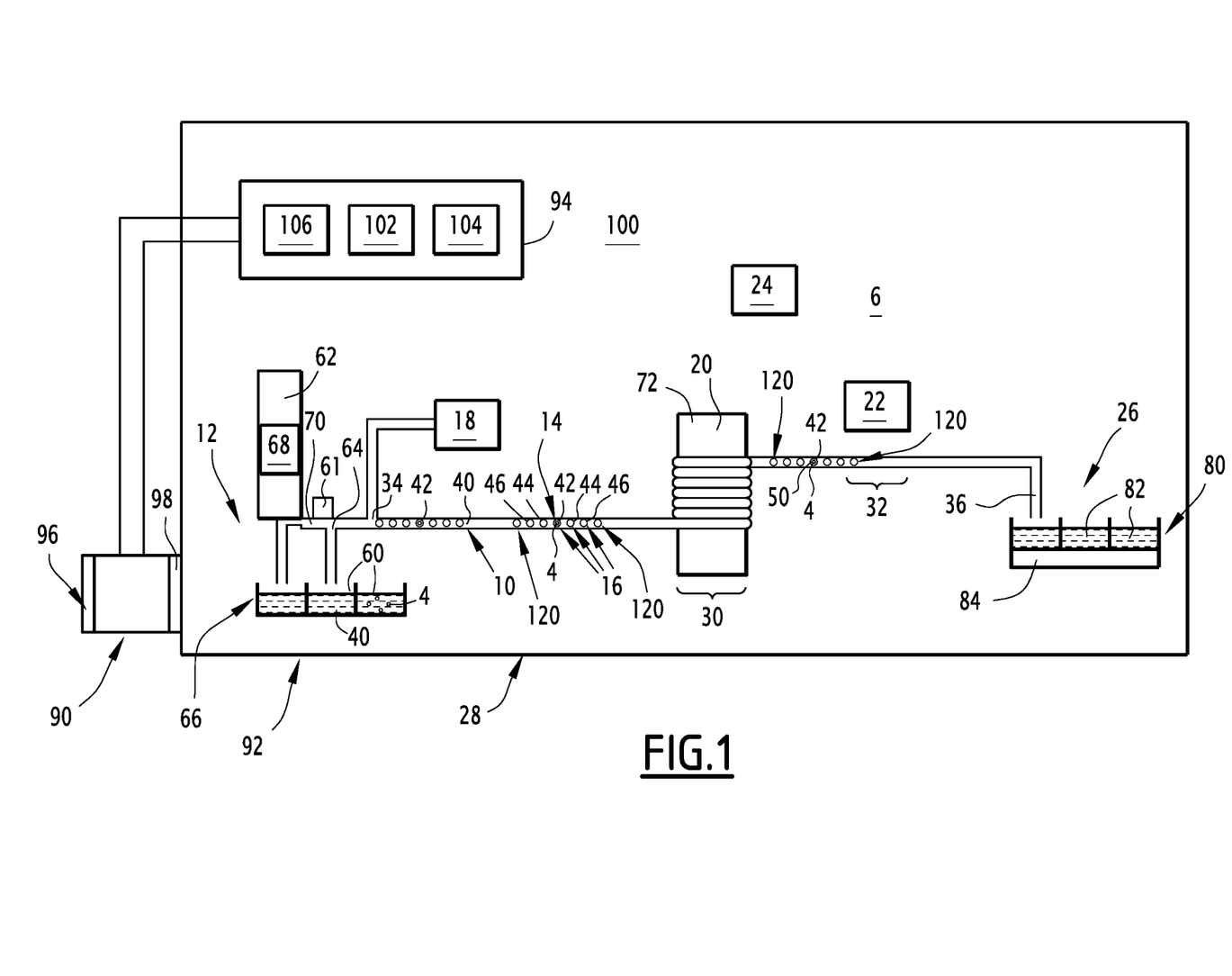
FIG. 1 is a schematic illustration of a first analysis and cell culture system according to the invention.

FIG. 1 illustrates a first analysis and cell culture system.

The first analysis and cell culture system 1 is a system for cultivating, analyzing and recovering cells 4 in a controlled atmosphere 6.

The cells 4 are for example microorganisms such as bacteria, yeasts, algae or filamentous fungi. The cells 4 are for example prokaryotic or eukaryotic cells.

The cells 4 are for example strictly anaerobic, that is to say, cells that die when they are exposed to dioxygen at atmospheric content, and can indifferently use fermentation or anaerobic respiration.

In a variant, the cells 4 are optionally anaerobic, that is to say, cells that can use dioxygen in the presence of the culture medium. In the presence of oxygen, these cells 4 can use aerobic respiration, whereas in the absence of oxygen, some of these organisms ferment and some perform anaerobic respiration.

In a variant, the cells 4 are microaerophiles, that is to say, cells that can use oxygen, but in minimal concentrations (in the order of a µmol); their development is inhibited under normal oxygen concentration conditions (close to 200 µmol). These cells primarily use aerobic respiration, although some may also use anaerobic respiration.

For example, the cells 4 come from cell lines. In a variant, the cells 4 come from collections. The collections are for example done within oil wells, an ice core, the bottom of an ocean or a living organism. For example, the cells 4 are intestinal bacteria. The cells are for example bacteria chosen from *Clostridium difficile, Mycobacterium tuberculosis* and *Nocardia asteroides*. In a variant, the cells 4 our soil bacteria, such as *Clostridium subterminale, C. sordeffii, C. sporogenes, C. indolis, C. bifermentans,* C. mangenoti, C. perfringen, C. Botulinum, or *C. tetani*.

A "controlled atmosphere" 6 refers to an atmosphere whose concentration in different gases is controlled, as will be described hereinafter. Advantageously, the controlled atmosphere 6 is devoid of oxygen and suitable for the survival of the studied cells 4.

The first analysis and cell culture system 1, according to the invention, includes a tube 10, a module 12 for generating a train 14 of drops 16 suitable for circulating in the tube 10, a circulating device 18 for the train 14 of drops 16 in the tube 10, an incubating device 20 for the train 14 of drops 16 in the tube 10, a measuring device 22, a central unit 24, a recovery device 26 and a control device 28 for the atmosphere.

The tube 10 is a capillary tube or fluid tube on the millimetric scale, that is to say, having an inner diameter in the order of a tenth of a millimeter to a millimeter, preferably between 0.5 and 2 mm.

The tube 10 has a rounded inner cross-section, such as circular or elliptical, or polygonal, such as rectangular.

The tube 10 has an incubating area 30 and a measuring area 32. Furthermore, the tube 10 has an inlet end 34 and an outlet end 36.

The module 12 for generating a train 14 of drops 16 is able to generate a train 14 of drops 16.

A train 14 of drops 16 is an ordered series of drops 16 in a carrier fluid 40.

The carrier fluid 40 is advantageously an organic phase, in particular an oily phase. The carrier fluid 40 for example comprises hydrofluoroethers such as FC-40 or HFE-7500, forming a fluorinated oil. In a variant, the carrier fluid 40 comprises a silicone oil or an organic oil such as mineral oil.

The carrier fluid 40 is capable of separating two successive drops 16 of the train 14 of drops 16.

The train 14 of drops 16 comprises at least one culture drop 42. Furthermore, as shown in FIG. 1, the train of drops comprises at least a test drop 44 and an absorption drop 46.

The train 14 of drops 16 advantageously comprises separators 120. A separator 120 is a gas bubble. For example, the gas composition in the separator 120 corresponds to the composition of the controlled atmosphere 6. The separator 120 promotes the spacing between two successive drops 16 of the train 14 of drops 16 to prevent the contact or fusion of the drops 16.

In an example that is not shown, the train 14 of drops 16 comprises a separator 120 between each drop 16.

Each drop 16 of the train 14 of drops 16 constitutes a closed compartment filled with internal fluid 48.

Each drop 16 comprises an inner fluid 48 that is not miscible with the carrier fluid 40. Immiscible means that the distribution coefficient between the two fluids is less than $10^{-3}$. The internal fluid 48 is advantageously an aqueous phase.

The volume of the drops 16 of the train 14 of drops 16 is for example between 100 nL and 2 µL.

In one example, the volume of the culture drops 42 is substantially the same from one culture drop 42 to the next.

The culture drop 42 comprises a culture medium 50 and at least one cell 4.

The culture medium 50 comprises a liquid culture medium suitable for the survival and growth of the cell 4 such as a buffered solution completed with culture nutrients, vitamins, electron donors and receivers. For example, the liquid culture medium 50 is Yeast extract-Casein hydrolysate-Fatty Acids (YCFA), Cooked Meat Broth (CMB), Chopped Meat Carbohydrate Broth, Columbia broth, blood culture medium, Brain-heart infusion medium (BHIM), or sheep stomach extract medium. For example, the culture medium 50 advantageously contains antibiotics.

Advantageously, the culture drop 42 further comprises a viability marker for the cells 4, such as calcein AM.

Advantageously, the culture drop 42 further comprises a growth indicator. For example, the indicator is carboxyfluorescein diacetate (CFDA) or an indicator of the presence of ATP using a luciferase.

The culture drop 42 further comprises elements secreted by the cell 4 such as proteins. Advantageously, the culture drop 40 comprises signal entities capable of indicating the presence of secreted elements and allowing their quantification. For example, the signaling entities are fluorogenic substrates that indicate the presence of an enzyme.

Advantageously, test drops 44 and absorption drops 46 are placed near each culture drop 42 in the train 14 of drops 16.

For example, the train 14 of drops 16 successively comprises, for each culture drop 42, an absorption drop 46, a test drop 44, said culture drop 42, a test drop 44 and an absorption drop 46. Thus, the test drops 44 frame the culture drop 42.

A test drop 44 makes it possible to verify the dissolved gas composition near the culture drop 42.

The test drop 44 comprises an oxygen indicator agent. The oxygen indicator agent is for example a colored indicator. The oxygen indicator agent is for example resazurin or MitoXpress® Xtra (Luxcel Biosciences). In a variant or additionally, the test drop 44 has other indicators making it possible to detect the presence of other gases.

The absorption drop 46 comprises an oxygen reducing agent. The reducing agent is for example able to reduce the dioxygen of the absorption drop 46. This oxygen reduction makes it possible to reduce the dissolved dioxygen level near the culture drop 42. The reducing agent for the oxygen dissolved in the water can be chosen among hydrazine or a salt thereof, alkaline or earth alkaline acid or neutral sulfites, such as sodium sulfate, nitrates, hyposulfites, thiosulfates, hydroxylamine, ascorbic acid, or a mixture of two or more thereof. Preferably, hydrazine hydrate will be used, which has the advantage of being an immediate reducer of the oxygen dissolved in water, at a low concentration.

In a variant, oxygen indicator and/or oxygen reducing agents are placed directly in the culture drop 42. These reducing agents will be able to be chosen from among cysteine, ascorbic acid or sodium thioglycolate.

The generating module 12 of the train 14 of drops 16 includes one or a plurality of reservoirs 60, a collection device 62 and an input circuit 64.

The generating module 12 further includes a complementary reservoir 61. The complementary reservoir 61 includes the carrier fluid 40.

Each reservoir 60 comprises a fluid necessary for the formation of the train 14 of drops 16.

For example, reservoirs 60 are different compartments of a microtitration plate 66. In a variant, the reservoirs 60 are test tubes such as Falcone tubes or micro-tubes like those sold by Eppendorf®.

A reservoir 60 comprises a suspension of cells 4. The concentration of the cells 4 in the reservoir 60 of cells 4 is advantageously suitable so that during the generation of the culture drops 42, the culture drops 42 comprise only one cell 4. For example, the concentration of cells 4 in the suspension is between $10^2$ and $10^5$ cells per milliliter.

For example, one reservoir 60 includes the culture medium 50. For example, other reservoirs 60 contain reagents to be placed in the culture drop.

For example, one reservoir 60 comprises an oxygen indicator agent.

For example, one reservoir 60 comprises an oxygen reducing agent.

The collection device 62 is capable of withdrawing solutions in each of the reservoirs 60 so as to form a train 14 of sequenced drops 16 in the carrier fluid 50, the train 14 of drops 16 comprising at least one culture drop 42.

The collection device 62 is capable of preparing the train of drops in the inlet circuit 64.

For example, the collection device 62 includes a robotic pipetting arm. In a variant or additionally, the collection device 62 includes a suction head. The use of a robotic collection device 62 makes it possible to limit the space necessary for manipulations.

For example, the collection device 62 comprises a gas reservoir 68. The gas of the reservoir 68 has a gas composition corresponding to the composition of the controlled atmosphere. The gas reservoir 68 is for example used to pressurize the various reservoirs 60, 61 in order to facilitate the collection. For example, the collection device 62 is capable of injecting a fluid into the inlet circuit 64 by pushing the fluid from the reservoir 60, 61 using gas into the inlet circuit 64.

In a variant or additionally, the collection device 62 includes a suction pump placed at the outlet 36. The pump is capable of suctioning the different fluids and placing the reservoirs 60, 61 under a vacuum. For example, the pump is a compressor or a gerotor pump.

The collection device 62 advantageously comprises a robot capable of preparing the content of the reservoirs 60 in the enclosure.

The inlet circuit 64 is connected to the inlet 34 of the tube 10. The inlet circuit 64 includes a splitting device 70 capable of generating drops 16 from the collected suspension and a carrier fluid 40.

For example, the inlet circuit 64 comprises a recess or a step facilitating the splitting of the fluids and the generation of the drops 16. In a variant, the inlet circuit 64 comprises a flow focusing junction, or a T junction.

The carrier fluid 40 is for example injected, at the inlet circuit 64, along the suction tube 10 by the injection device so as to form the drops 16 of the train of drops by co-flow.

The device for circulating 18 the train 14 of drops 16 is capable of moving the train 14 of drops 16 within the tube 10 from the inlet 34 to the outlet 36.

The circulating device 18 for example comprises a blower unit and/or a suction unit.

The circulating device 18 is advantageously capable of circulating the train 14 of drops 16 from the incubating area 30 to the measuring area 32, then from the measuring area 32 to the incubating area 30. The drops 16 can thus be moved in both directions in the tube 10.

For example, the measuring area 32 is located downstream from the incubating area 30. The circulating device 18 is able to take the culture drop 42 from the incubating area 30 to the measuring area 32 in order to measure the parameter indicative of the content of the culture drop 42. The circulating device 18 is also able to take the culture drop 42 from the measuring area 32 to the incubating area 30 in order to continue the incubation of the culture drop 42.

The circulating device 18 is capable of generating a flow rate of the train 14 of drops 16 and carrier fluid 40 in the tube of between 0.1 mL/h and 5 mL/h.

The incubating device 20 is capable of inspecting the temperature of the incubation area 30 of the tube 10. For example, the incubating device 20 is capable of heating or cooling the incubation area 30 of the tube to a temperature of between 4° and 100° C., for example between 20° C. and 50° C., and in particular at 37° C. In one example, in order to cultivate and analyze microorganisms associated with human pathologies, the temperature is set to 37° C.

The incubating device 20 comprises a coil 72 able to be temperature-regulated, the part of the tube 10 corresponding to the incubating area 30 being wound around the coil 72. This winding makes it possible to reduce the necessary bulk in order to have a large incubation length.

For example, the length of tube 10 wound in the incubation area 30 is between 10 meters and 100 meters.

In a variant, the incubating device comprises a chamber delimited by thermally insulating walls, a heating and cooling element such as a Peltier module, a fan making it possible to circulate the content convection gas and a temperature probe.

The measuring device 22 is capable of measuring a parameter indicative of the content of the culture drop 42 in the tube 10 at the measuring area 32 at different times.

For example, the parameter is representative of the growth of a clone in the drop or of the survival of the cells. Such successive measurements make it possible to produce, for each culture drop, curves of growth kinetics within the drop during the incubation.

For example, the measuring device is capable of performing an optical density measurement, a light diffusion measurement and/or an analysis on an image of a drop.

In a variant or additionally, the measuring device 22 is capable of detecting or quantifying a protein.

For example, the measurement is an optical measurement, such as a fluorescence measurement.

Advantageously, the measuring device 22 is capable of measuring the oxygen level in a drop 16. For example, the measurement of the oxygen level is done by detecting the oxygen indicator agent.

The central processing unit 24 includes a memory and a microprocessor. The central processing unit 24 is capable of recording the data from the measuring device 18 for each culture drop 42.

The central processing unit 24 is capable of analyzing the measurements done for a culture drop 42 and checking the recovery of the culture drop 42 or the continued incubation depending on the result of the analysis.

The recovery device 26 is capable of allowing the recovery of each drop 16 individually.

The recovery device 26 for example comprises a recovery container 80 comprising several compartments 82, and a movement device 84 for moving the recovery container 80 relative to the outlet 36 of the tube 10 such that a new compartment 82 is placed across from the outlet 36 of the tube for each drop 16 to be recovered.

The device for controlling the atmosphere 28 is able to control the atmosphere 6 in the culture analysis system.

The controlled atmosphere 6 is an atmosphere suitable for the cells.

The controlled atmosphere 6 is for example an anaerobic atmosphere. For example, the controlled atmosphere 6 is stabilized at 85% dinitrogen and 15% carbon dioxide. An anaerobic atmosphere is an atmosphere not comprising oxygen.

In a variant or additionally, the controlled atmosphere 6 comprises hydrogen. The composition can then be 85% dinitrogen, 10% carbon dioxide and 5% dihydrogen.

The device for controlling the atmosphere 28 includes an airlock 90, a closed chamber 92 and a regulating device 94.

The airlock 90 makes it possible, for example, to introduce a plate 66 with the different reservoirs 60, an additional reservoir 61 containing the carrier fluid degassed beforehand, or to recover the recovery container 80.

In a variant or additionally, the airlock 90 makes it possible to refill the reservoirs 60 with liquids or gases.

The airlock 90 defines an inner volume with a controlled atmosphere and includes an outer door 96 and an inner door 98. Each door 96, 98 is movable between an open position and a closed position.

The outer door 96 makes it possible, in the open position, to introduce components into the airlock 90 or to remove components from the airlock 90. The outer door 96 is able to isolate the atmosphere of the airlock 90 from the outside atmosphere in the closed position.

The airlock 90 is connected to the chamber 92 by the inner door 98. The inner door 98 makes it possible, in the open position, to introduce components from the airlock 90 into the chamber 92 or to introduce components from the chamber 92 into the airlock 90. The inner door 98 is able to isolate the atmosphere of the airlock 90 from the atmosphere of the chamber 92 in the closed position.

The chamber 92 defines an inner volume 100 with a controlled atmosphere 6.

In one example, the chamber 92 is a glove box. The gloves make it possible to act manually, for example, to prepare the reservoirs before the formation of the train of drops or to seal or unseal a container, in order to move the recovery container 80 toward the airlock 90.

In a variant, the chamber 92 is a carcass closed without gloves and a robot makes it possible to automate the operations performed manually.

The regulating device 94 is able to control the atmosphere 6 in the chamber 92 and the airlock 90. The regulating device 94 is able to inject a gas into the inner volume 100 as a function of the partial pressure of the different gases contained in the inner volume 100.

The regulating device 94 for example comprises, for each gas of the controlled atmosphere, a sensor 102 and a gas reserve 104.

In a variant, the regulating device 94 includes a single gas reserve 104 comprising, with the mixture, gases in proportions corresponding to the proportions in the controlled atmosphere 6.

In addition, the control device 28 for controlling the atmosphere advantageously comprises an oxygen detector 106.

The device comprises a system for eliminating residual oxygen comprising a catalyst.

In the first analysis and culture system 1, the tube 10, the generating module 12 for generating the train 14 of drops 16, the circulating device 18 for circulating the train 14 of drops 16, the incubating device 20 for incubating the train 14 of drops 16, the measuring device 22 and the recovery device 26 are arranged in the inner volume of the chamber 92.

The outer dimensions of the control device 28 are thus the outer dimensions of the first analysis and cell culture system 1.

Advantageously, the dimensions of the control device 28 are such that it can be arranged on a lab table. In one example, the control device 28 measures 1452 mm long, 1056 mm deep and 993 mm high. In another example, the control device 28 measures 810 mm long, 760 mm deep and 635 mm high.

The analysis and cell culture method will now be described.

The method comprises supplying a first analysis and cell culture system.

Advantageously, the method comprises a step for preparing the system for analysis.

During this step, the gas composition of the inner volume 100 of the chamber 92 is verified and regulated to be at the controlled atmosphere 6.

The reservoirs 60 are for example sealed and introduced into the chamber 92 by the airlock 90. They are next unsealed once they are in the chamber 92.

The reservoirs 60 containing the liquids to be used are for next left 24 hours in the chamber 92 of the control device 28 in order to balance the dissolved gases.

In a variant, the reservoirs 60 are prepared in the chamber before generating the train 14 of drops 16. For example, this preparation is manual; in a variant, it is done by a robot.

The method further comprises generating an ordered train 14 of drops 16 in a carrier fluid 12, circulating the train 14 of drops 16 in the tube 10, incubating the train 14 of drops 16, measuring at least one parameter indicative of the content of the culture drop 42 in the tube 10 at different moments during the incubation and recovering the culture drop 42 at one end 36 of the tube 10, the steps being done in a controlled atmosphere 6.

The train 14 of drops 16 is generated by the generating module 12 of the train of drops.

For example, the train 14 of drops 16 is circulated at a flow rate of 1 mL/h.

The incubating area 30 of the tube is kept at a temperature of 37° C.

The incubation is done in the incubating area 30 of the tube 10.

The incubation is done by successive phases; a measurement is done at the end of each incubation phase.

Advantageously, each incubation phase lasts 30 minutes.

For example, in total, the incubation lasts between 4 hour and 72 hours.

During the measuring step, the culture drop 42 is placed in the measuring area 32. The measurement for example comprises measuring a fluorescence signal indicative of the growth of a clone in the culture drop 42.

Advantageously, the measurement further comprises measuring the oxygen level in the culture drop 42 or in the test drop 44. For example, the measurement of the oxygen level is done by detecting the oxygen indicator agent.

Advantageously, the method further comprises a step for analysis of the measurements done for the culture drop 42, the recovery of the culture drop or the continuation of the incubation depending on the results of the analysis. This step is carried out by the central processing unit 24.

Advantageously, the growth speed is determined by the central processing unit 18, the culture drop 42 is recovered after slowing of the growth of the clone.

For example, when it is detected in the culture drop 42 that a molecule is produced by a cell 4 or a cell population, the culture drop 42 is recovered in the recovery substrate 80.

If the measurement corresponds to a selection criterion of the user, for example when it is measured while the clone is still in the growth acceleration phase, the culture drop 42 is returned to the incubating area 30 by the circulation device 18. The criterion is, for example, a final biomass quantity or a growth speed. For example, when it is detected that the culture drop 42 does not comprise cells, the culture drop 42 is discharged. Likewise, if the measurement does not correspond to the selection criteria of the user, the culture drop 42 is discharged.

The method thus makes it possible to isolate cells, during the formation of the train of drops, to cultivate them in a controlled atmosphere and to perform a verification during the culture of the cells, then to sort and recover the obtained clones in isolation.

In this system, all of the elements of the system being contained in the chamber 92, the verification of the quality of the atmosphere 8 is simplified.

Figure 2:
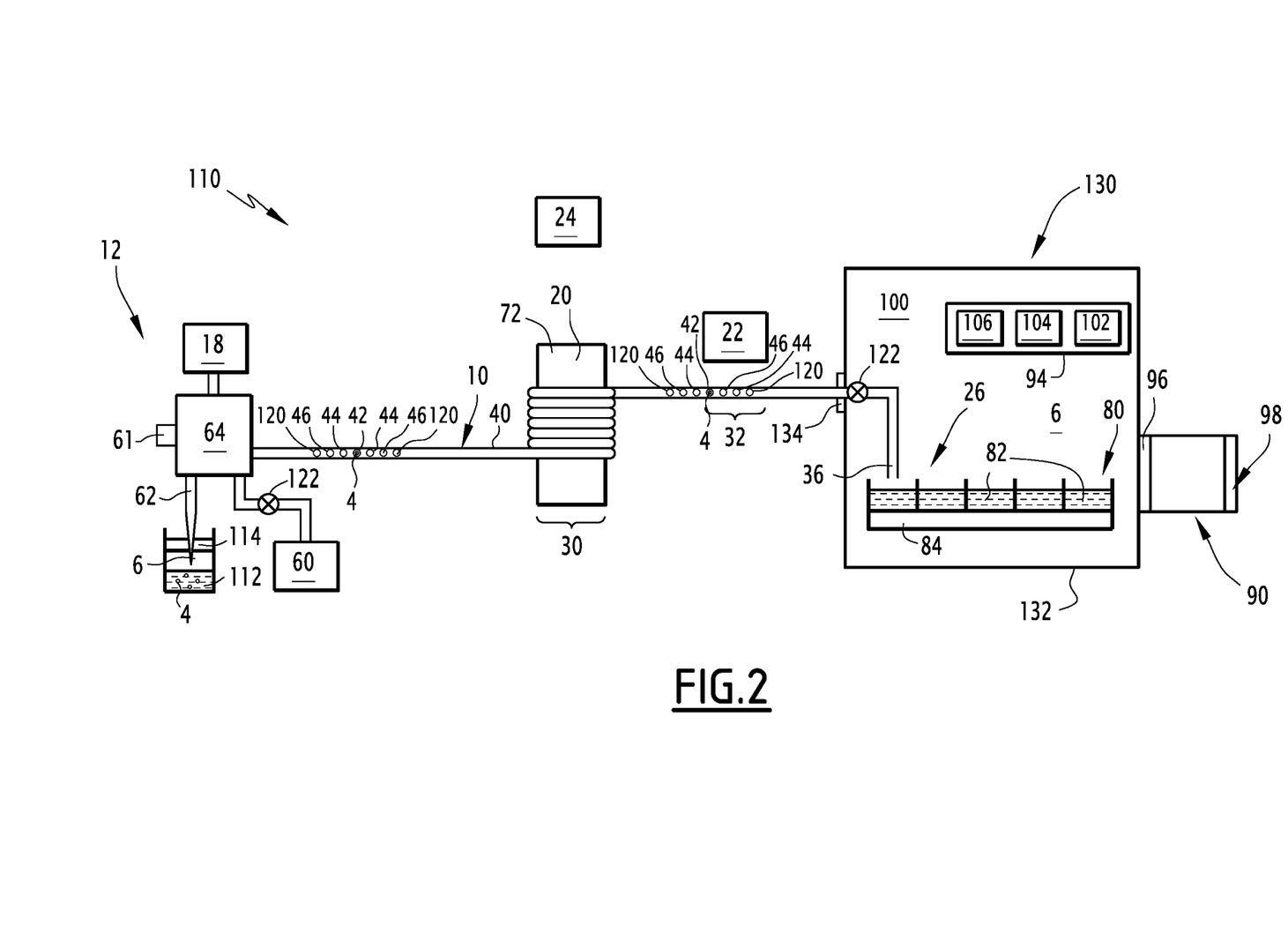
FIG. 2 is a schematic illustration of a second analysis and cell culture system according to the invention.

A second analysis and cell culture system 110 will the described in light of FIG. 2. Only the differences with respect to the first system 1 will be described. The second analysis and cell culture system 110 differs from the first analysis and cell culture system 1 in that the tube 10 is impermeable to gases.

The tube 10 is in particular impermeable to oxygen, which makes it possible to avoid contaminating the internal environment of the tube 10 by its walls.

In this second system, the cell reservoir 112 comprising the suspension of cells 4 is sealed by a septum 114.

For example, the other reservoirs 60, 61 are sealed and degassed canisters. For example, a quality indicator is added into each liquid.

Advantageously, the inner volume of each reservoir 60, 72 is closed and shows the atmosphere shows the composition of the controlled atmosphere 6.

The reservoirs 60, 61 are pressurized by injecting a gas, the composition of which is controlled.

Furthermore, the collection device 62 is able to pierce the septum 114 to collect part of the suspension of cells 4.

The inlet circuit 64 and the tube 10 comprise solenoid valves 122.

Each solenoid valve 122 is impermeable and able to fluidly isolate two parts of the inlet circuit 64 from one another, or two parts of the tube 10 from one another, or the inlet circuit 64 from the tube 10.

For example, the second system 110 advantageously comprises a solenoid valve 122 at each inlet of the inlet circuit 64 and a solenoid valve 122 before the area for generating drops 16.

For example, a solenoid valve 122 separates the measuring area from the outlet 34 of the tube 10.

In the part in contact with the carrier fluid 40, the solenoid valve 122 is made from a material compatible with the carrier fluid 40.

For example, each solenoid valve is made from EPDM (ethylene-propylenediene-diene monomer).

When the circulating device 18 includes a blower unit, the latter blows a gas in the composition of the controlled atmosphere 6.

The atmosphere control device 130 comprises a chamber 132 with a controlled atmosphere containing the recovery device 26. The chamber 132 is similar to the chamber 92 previously described. Advantageously, the atmosphere control device 130 comprises an airlock 90 connected to the chamber 132 and a regulating device 94 as previously described.

The volume of the chamber 132 is between 0.4 m$^3$ and 1.5 m$^3$.

The tube 10 is provided with a sealing gasket 134 between the outer part of the chamber and the inner part of the chamber.

The analysis and cell culture method with the second system 110 differs from the method previously described in that during the step for preparation of the second system, a gas, the composition of which is controlled, is injected into the tube 10. The preparation step is done before the step for generating the train 14 of drops 16.

The gas introduced into the tube 10 is pushed to the outlet 36 in order to eliminate the oxygen residues before the operation.

An outlet container is connected at the outlet. For example, the outlet container is detached under a constant gas stream to prevent air from entering through the outlet.

In order to verify that there has not been any contamination, the sealing of the system is verified before the circulation or after the recovery.

Furthermore, the indicators make it possible to verify the oxygen level during the incubation.

This second system 110 allows a limited gas consumption for the control of the atmosphere 6. Indeed, the volume of the chamber is limited, since it only comprises the recovery area.

In a variant of the second system 110, the reservoirs 60 are different compartments of a micro-titration plate. The plate is for example prepared and sealed upstream in a controlled environment.

In a variant of the second system, the carrier fluid 40 comprises a fluorinated oil. The core of the tube 10 is made from PTFE, this material being compatible with the fluorinated oil and transparent. PTFE not being completely impermeable to oxygen, the tube is covered with an outer sheath. The outer sheath is impermeable to oxygen. Advantageously, the outer sheath is transparent to allow the measurement. In a variant, the core of the tube is made from FEP (Fluorinated ethylene propylene).

A third analysis and cell culture system 140 will the described in light of FIG. 2. Only the differences with respect to the second system 1 will be described. The second analysis and cell culture system 140 differs from the first analysis and cell culture system 1 in that the recovery and preparation areas are made in a same chamber 132. Thus, the same reservoirs as in the embodiment of FIG. 1 can be used.

Figure 3:
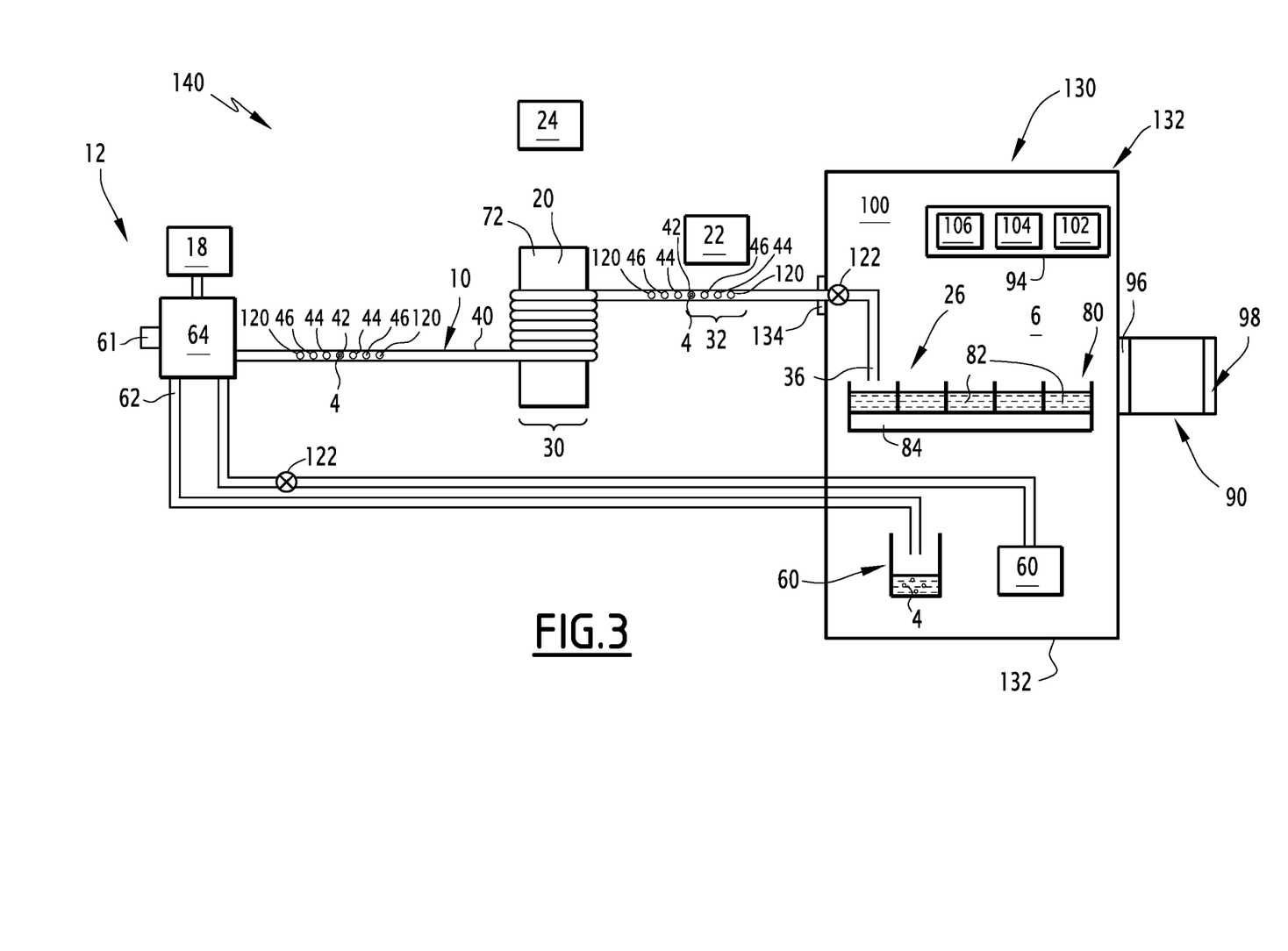
FIG. 3 is a schematic illustration of a third analysis and cell culture system according to the invention.

In a variant of the third analysis system 140, the same robot and the same tip are used for the preparation and recovery steps. For example, one of the ends 34, 36 of the tube 10 is used as both inlet end and outlet end.

A fourth analysis and cell culture system 200 will the described in light of FIG. 3. Only the differences with respect to the second system 1 will be described. The fourth analysis and cell culture system 200 differs from the second analysis and cell culture system 110 in that the parts of the tube 10 not extending in a chamber with a controlled atmosphere are covered by an impermeable sheath 202.

Figure 4:
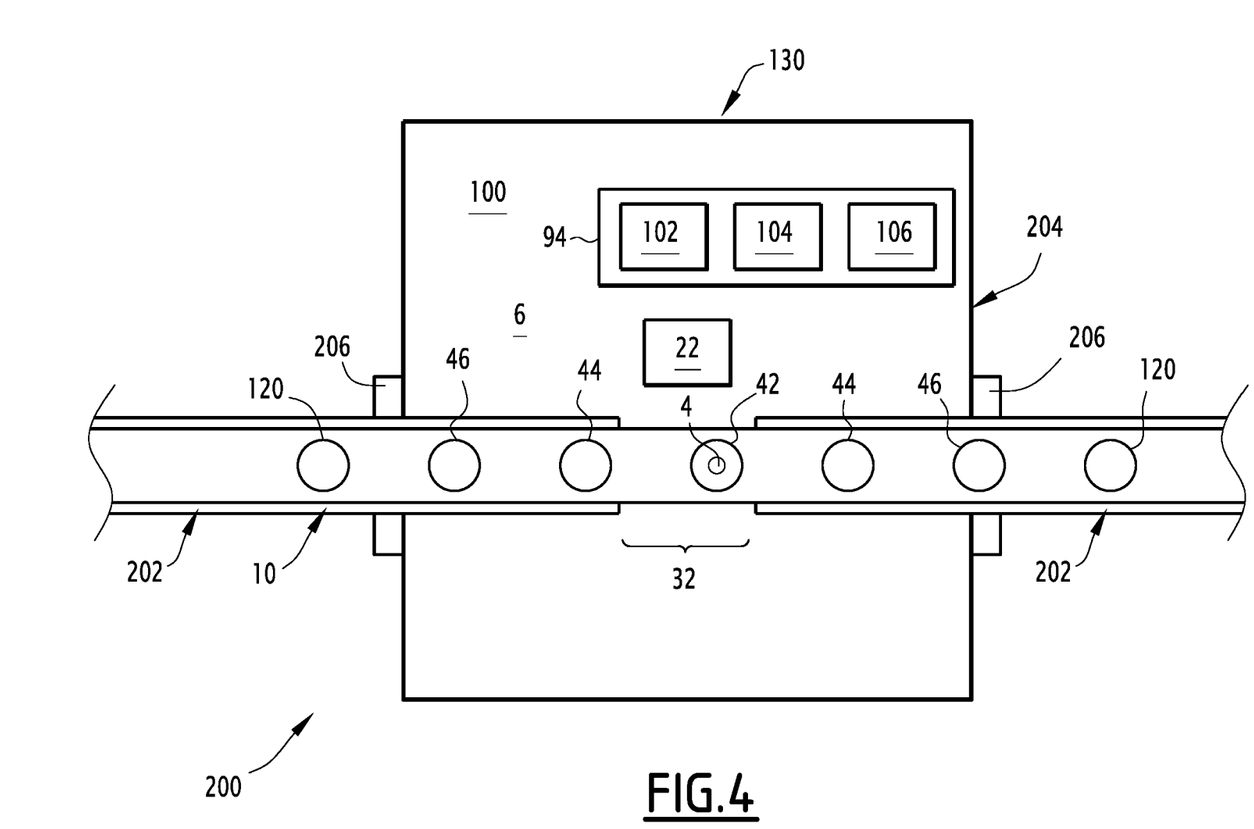
FIG. 4 is a view of part of a fourth analysis and cell culture system according to the invention.

For example, the impermeable sheath 202 is made from metal.

The sheath 202 is undone at the measuring area 32. The measuring area 32 of the tube 10 is placed in a chamber with a controlled atmosphere 204. The chamber 204 is similar to the chamber 92 previously described. Advantageously, the atmosphere control device 130 comprises a regulating device 94 as previously described able to regulate the atmosphere in the chamber 204.

The measuring device 22 is arranged in the chamber with a controlled atmosphere 204. The chamber 204 is advantageously opaque to prevent outside light from arriving in the measuring area 32. Furthermore, the chamber 24 makes it possible to control the atmosphere in the measuring area 32.

The tube 10 includes a sealing gasket 206 at the inlet and outlet of the chamber 202 of the measuring area 32. In another embodiment, the cell culture and analysis system comprises a plurality of coils 72. This makes it possible to perform several incubations in parallel. This is particularly advantageous when the cultures are very slow. An additional spool makes it possible to store the drops 16 during incubation.

In another embodiment, the cell culture and analysis system allows the selection of a drop 16 during the incubation and its circulation in a bypass circuit. For example, the incubation conditions in the bypass circuit are different.

One advantage of the cell culture and analysis system 1, 110, 140, 200 is that it makes it possible to detect clone formation and to measure metabolite production.

The invention allows the automated, miniaturized and high-throughput performance of the culture, isolation, and screening for cells requiring a controlled environment.

Furthermore, the nature of the controlled atmosphere can easily be modified to perform certain biological studies or to best optimize clone growth.

The invention claimed is:

1. A method for analysis and cell culture comprising:
   generating a train of ordered drops in a carrier fluid, the train of drops comprising at least one culture drop, the at least one culture drop comprising a culture medium and at least one cell,
   circulating the train of drops in a tube having a measuring area,
   incubating the train of drops in the tube,
   measuring at least one parameter indicative of the content of the at least one culture drop in the tube at different times,
   recovering the at least one culture drop at one end of the tube,
   the method being carried out in a controlled atmosphere wherein the method further comprises measuring the parameter indicative of the content of the at least one culture drop at different times at the measuring area, and placing the measuring area of the tube in a chamber with a controlled atmosphere so that the parts of the tube not extending in a chamber with controlled atmosphere are covered by an impermeable sheath.

2. The method for analysis and cell culture according to claim 1, further comprising analysis of the measurements done for the at least one culture drop, the recovery of the at least one culture drop or the continuation of the incubation depending on the results of the analysis.

3. The method for analysis and cell culture according to claim 1 wherein the controlled atmosphere is an anaerobic atmosphere.

4. The method for analysis and cell culture according to claim 1 wherein the at least one parameter is a parameter indicative of a growth of a clone in the at least one culture drop.

5. The method for analysis and cell culture according to claim 1 further comprising preparing a system in which a gas, the composition of which is controlled, is injected into the tube before generating the train of ordered drops.

6. An analysis and cell culture system comprising:
   a tube,
   a generating module for generating a train of ordered drops in a carrier fluid the train of drops comprising at least one culture drop, the culture drop comprising a culture medium and at least one cell,
   a device for circulating the train of drops in the tube,
   a device for incubating the train of drops in the tube,
   a measuring device able to measure at least one parameter indicative of the content of the at least one culture drop in the tube at different times,
   a device for recovering the at least one culture drop at one end of the tube, and
   a device for controlling an atmosphere able to control the atmosphere in the analysis and culture system;
   wherein the tube has a measuring area, the measuring device is able to measure the parameter indicative of the content of the at least one culture drop at different times at the measuring area, and the measuring area of the tube is placed in a chamber with a controlled atmosphere so that the parts of the tube not extending in a chamber with controlled atmosphere are covered by an impermeable sheath.

7. The analysis and cell culture system according to claim 6, wherein the device for controlling the atmosphere comprises a chamber with a controlled atmosphere containing the generating module the circulating device the tube the incubating device the measuring device and the recovery device.

8. The analysis and cell culture system according to claim 6, wherein the tube is impermeable to gases, the device for controlling the atmosphere comprising a chamber with a controlled atmosphere containing the recovery device at least part of the tube being arranged outside the chamber with a controlled atmosphere.

9. The analysis and cell culture system according to claim 6 wherein the train of drops comprises at least one drop comprising an oxygen indicator agent.

10. The analysis and cell culture system according to claim 6 wherein the train of drops comprises at least one drop comprising an oxygen reducing agent.

11. The analysis and cell culture system according to claim 6 wherein the incubating device comprises a coil able to be temperature-regulated, part of the tube being wound around the coil.

12. The analysis and cell culture system according to claim 11, wherein the generating module comprises:
    a reservoir comprising a suspension of cells in an anaerobic atmosphere, the reservoir being sealed by a septum,
    a collection device able to pierce the septum to collect part of the suspension.

13. The analysis and cell culture system according to claim 6 comprising at least one impermeable solenoid valve able to isolate two parts of the tube from one another.

* * * * *